United States Patent [19]

Kummer et al.

[11]  4,110,470
[45] * Aug. 29, 1978

[54] PHARMACEUTICAL COMPOSITION COMPRISING D,L-α-METHYL-THYROXINE ETHYL ESTER AND THE SALTS THEREOF AND THE CONTROL OF CHOLESTEROL AND TRIGLYCERIDE BLOOD LEVEL THEREWITH

[76] Inventors: Horst Kummer, Rheinecke 14, 67 Ludwigshafen am Rhein; Rüediger Beckmann, Elsa-Brandstroem-Strasse 10, 51 Aachen, both of Fed. Rep. of Germany

[ * ] Notice: The portion of the term of this patent subsequent to Dec. 30, 1992, has been disclaimed.

[21] Appl. No.: 178,780

[22] Filed: Sep. 8, 1971

Related U.S. Application Data

[60] Continuation-in-part of Ser. No. 38,647, May 22, 1970, Pat. No. 3,930,017, and Ser. No. 77,744, Oct. 2, 1970, abandoned, said Ser. No. 38,647, is a division of Ser. No. 584,089, Oct. 4, 1966, which is a continuation of Ser. No. 584,089.

[30] Foreign Application Priority Data

Oct. 7, 1965 [DE] Fed. Rep. of Germany ....... 1493567

[51] Int. Cl.$^2$ ............................................. A61K 31/24
[52] U.S. Cl. .................................................. 424/309
[58] Field of Search ........................................ 424/309

[56] References Cited

U.S. PATENT DOCUMENTS 3,410,891  11/1968  Hughes et al. ........................ 260/471
3,930,017  12/1975  Kummer et al. ...................... 424/309

FOREIGN PATENT DOCUMENTS 859,546  1/1961  United Kingdom ..................... 424/309

Primary Examiner—Frederick E. Waddell
Attorney, Agent, or Firm—Weiser, Stapler & Spivak

[57] ABSTRACT

The invention relates to a new pharmaceutical composition and a method of treating patients.

19 Claims, No Drawings

PHARMACEUTICAL COMPOSITION COMPRISING D,L-α-METHYL-THYROXINE ETHYL ESTER AND THE SALTS THEREOF AND THE CONTROL OF CHOLESTEROL AND TRIGLYCERIDE BLOOD LEVEL THEREWITH

This is a continuation-in-part application of application Ser. No. 38,647, filed May 22, 1970, of Ser. No. 77,744, filed Oct. 2, 1970, which are a divisional application and a continuation application, now abandoned, respectively, of patent application Ser. No. 584,089, filed Oct. 4, 1966, and now abandoned; application Ser. No. 38,647 is now U.S. Pat. No. 3,930,017, issued Dec. 30, 1975.

The invention relates to a new pharmaceutical composition and a method of treating patients suffering from organic malfunctions.

As confirmed by clinical and pathological observations, sclerosis of blood vessels is rarely observed in patients with hyperfunctioning thyroid glands. Therefore, many attempts have been made to favorably influence arteriosclerosis and in particular coronary sclerosis by the administration of thyroid hormones. In animal experiments, such favorable effect can be demonstrated by a lowering of the lipid and especially the cholesterol serum level. An adverse reaction encountered upon the administration of thyroid hormones which reduces the usefulness of these hormones and/or makes their administration at least in coronary sclerosis contra-indicated, is the increase in the basal metabolic rate. The basal metabolic rate of male rats, for example, determined by the increase in oxygen consumption, is raised significantly on subcutaneous application of 0.01 mg/kg of L-thyroxine.

From Irish Pat. No. 365/65 it is known that, on introducing alkyl radicals in the alpha-position of certain thyronine derivatives, compounds are obtained which are capable of lowering the cholesterol and lipid level without raising the basal metabolic rate. If, for example, rats which have been fed on a cholesterol-rich diet are given subcutaneously 1000 νkg of d,l-alpha-methyl thyroxine sodium daily for a period of 14 days, the serum cholesterol level of the thus treated rats is lowered from 380 to 265 mg%. When measuring the basal metabolic rate of rats, subcutaneous administration of 4 mg./kg. of dl-α-methyl thyroxine does not cause an increase in oxygen consumption. In comparison to L-thyroxine dl-α-methyl thyroxine only slightly increases oxygen consumption and only after increasing the dose 2000 times.

The antigoitrogenic activity, i.e. remission of the thyroid gland enlargement in rats caused by the administration of thiouracil, may be considered an additional criterion for the undesired thyreomimetic activity of a tested compound. In this test, 20 mg. of dl-α-methyl thyroxine correspond in their activity to 0.020 mg. of L-thyroxine. A reduction in the weight increase as it is observed after administration of thyroid hormones on account of the thyreotoxic activity of these compounds, has not been observed after administration of dl-α-methyl thyroxine. Thus the final body weight of rats to which 4.0 mg./kg. of α-methyl thyroxine has been administered daily for a period of 14 days is the same as that of dietary controls.

However, the dl-α-methyl thyroxine or, respectively its salts as it has become known from the said Irish patent have the disadvantage of being inactive on oral administration.

It is now an object of the present invention to provide new and valuable α-alkyl thyronine compounds which are highly effective agents capable of lowering the cholesterol and lipid level in the blood without raising the blood metabolic rate and which can be administered not only parenterally but also orally.

Another object of the present invention is to provide a simple and effective process of producing such α-alkyl thyronine compounds.

A further object of the present invention is to provide valuable compositions containing such α-alkyl thyronine compounds as active, cholesterol and lipid level-decreasing agents.

Still another object of the present invention is to provide a process of lowering the cholesterol and lipid blood level in persons suffering from a high cholesterol and lipid blood level.

Other objects of the present invention and advantageous features thereof will become apparent as the description proceeds.

In principle the new and valuable α-alkyl thyronine compounds according to the present invention are new esters of α-alkyl thyronine compounds of the following Formula I

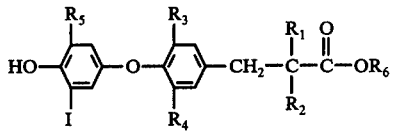

wherein
  $R_1$ indicates a linear or branched alkyl radical containing 1 to 6 carbon atoms;
  $R_2$ indicates the amino group or an acylated amino group;
  $R_3$, $R_4$, and $R_5$ represent the same or different substituents, namely hydrogen or iodine atoms; and
  $R_6$ represents an unsubstituted or substituted linear or branched alkyl radical containing 1 to 6 carbon atoms or an unsubstituted or substituted cycloalkyl or aralkyl radical,
as well as the addition salts of these compounds with inorganic or organic bases or acids.

A preferred substituent of the substituent $R_6$ is the amino group

wherein $R_7$ and $R_8$ are the same or are different substituents and represent hydrogen, lower alkyl, or, together with the nitrogen atom to which they are attached, a heterocyclic ring, which may be interrupted by other hetero atoms. Such heterocyclic rings are, for instance, the pyrrolidine, piperidine, morpholine-, or 4-alkyl piperazine ring.

As is evident from Formula I, the compounds of said formula contain one asymmetric carbon atom which bears four different substituents. Due to this configuration the compounds may form two optically active modifications. Resolving of the dl-compound into the two optically active forms is effected by methods known per se. Moreover, optically active forms of the compounds of Formula I can be obtained by using optically active starting materials for their preparation.

The new compounds of Formula I are obtained by reacting an acid, a salt, or a reactive derivative of the acid, for instance, a halogenide or an anhydride of an acid of Formula II

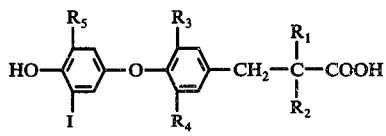

wherein
$R_1$ to $R_5$ represent the same substituents as indicated above,
with a compound of Formula III $$Y - R_6 \qquad \text{III}$$

wherein
$R_6$ represents the same substituent as indicated above and
Y represents a hydroxyl group, an esterified hydroxyl group, halogen or a hydroxyl group, in which the hydrogen atom is replaced by a metal atom.

Stoichiometric amounts of compounds of Formulas II and III may be used but also an excess of one of said reactants. Preferably esterifying catalysts of an acidic nature are added in the event that the compound of Formula II is not used in the form of its salt with a base or that the other reactant is not a compound of Formula III, in which Y represents a hydroxyl group wherein the hydrogen atom is replaced by a metal atom. In those instances whereby, on preparing a compound of Formula I, an acid is liberated, basic agents are preferably added to accelerate the reaction or to bind the acid. If, on reacting a compound of Formula II with a compound of Formula III, water is set free, such water may be removed by means of azeotropic distillation.

The compounds of Formula I can also be obtained by saponifying under esterifying conditions the nitrile group of a compound of Formula IV

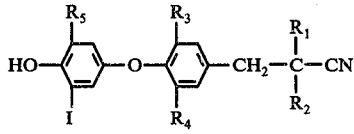

wherein
$R_1$ to $R_5$ represent the same substituents as indicated above
in the presence of acidic catalysts and of a compound of Formula V $$R_6 - OH \qquad V$$

wherein
$R_6$ represents the same substituents as indicated above.

Stoichiometric amounts of said compounds of Formulas IV and V may be used as well as an excess of the compound of Formula V. The intermediate imino ether salts obtained thereby may be isolated and transformed into compounds of Formula I in a separate reaction step.

Compounds of Formula I can also be obtained by subjecting a compound of Formula VI

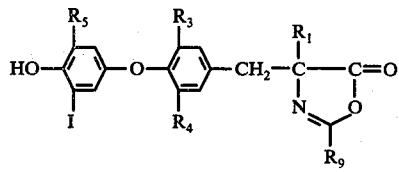

wherein
$R_1$ and $R_3$ to $R_5$ represent the same substituents as indicated above and
$R_9$ represents alkyl or ar[alky]l,
to alcoholysis at room temperature or at elevated temperature with a compound of Formula V, if required, with the addition of acids or bases as catalysts thereby yielding a compound of Formula VII

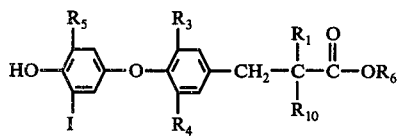

wherein
$R_1$ and $R_3$ to $R_6$ represent the same substituents as indicated above and
$R_{10}$ represents an acylated amino group,
and then converting the substituent $R_{10}$ into an amino group, if desired.

Furthermore, compounds of Formula I can be obtained by transforming the carboxamide group of a compound of Formula VIII

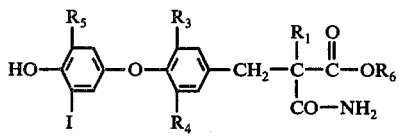

wherein
$R_1$ and $R_3$ to $R_6$ represent the same substituents as indicated above,
by means of a Hofmann rearrangement reaction into an amino group.

The compounds of Formula I can also be obtained by reacting a compound of Formula IX

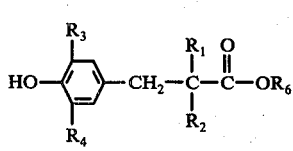

wherein
$R_1$ to $R_4$ and $R_6$ represent the substituents as indicated above,
at approximately neutral pH-values, preferably at a slightly basic pH-value with an acid of Formula X

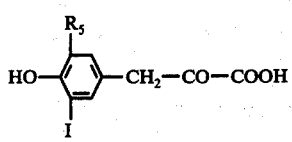

X wherein

R$_5$ represents the same substituent as indicated above.

This condensation reaction can be performed by dissolving a compound of Formula IX in a buffer solution, for example, in a solution of borax and disodium hydrogen phosphate, or in a solution of citric acid and disodium hydrogen phosphate or in other buffer solutions or mixtures, at a slightly basic pH-value, preferably at a pH of 7.6 to 7.8. These buffer solutions may have admixed thereto a water-soluble organic solvent such as a lower alkanol, dioxane, dimethyl formamide, dimethyl acetamide, ethylene glycol mono-ethyl ether, or mixtures of these organic solvents. The resulting solution of the compound of Formula IX is then reacted with a corresponding solution of an acid of Formula X. The solution of the acid of Formula X may be added at once or in portions. Stoichiometric amounts of the compounds of Formula IX and X may be used as well as an excess of one of said reactants. The condensation may also be carried out in the presence of a second organic solvent which is immiscible with water and forms a water-insoluble phase. Such solvents are, for instance, higher alcohols, chlorinated hydrocarbons, and aliphatic or aromatic hydrocarbons. Catalytically active compounds, such as organic peroxides or manganous salts may be added and the condensation may be effected at temperatures below 100° C. under anaerobic or aerobic conditions, for instance, by introducing oxygen into the reaction mixture.

The compounds of Formula I can also be obtained by condensing a reactive ester, preferably the p-tosyl ester, of a compound of Formula XI

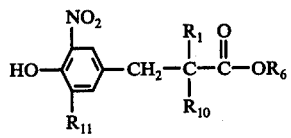

XI wherein

R$_1$, R$_6$ and R$_{10}$ represent the same substituents as indicated above and R$_{11}$ represents a nitro group or the substituent R$_4$, with a compound of Formula XII

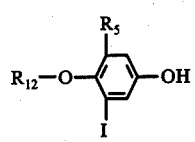

XII wherein

R$_5$ represents the same substituent as indicated above and the protecting group R$_{12}$ represents aralkyl which may be substituted, in the presence of a solvent and/or an inorganic or organic base, preferably pyridine, and, if required, at elevated temperature. Thereby, a compound of Formula XIII is obtained:

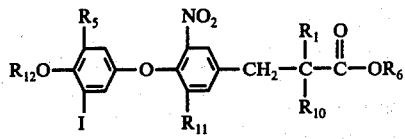

XIII wherein

R$_1$, R$_5$, R$_6$, and R$_{10}$ to R$_{12}$ represent the same substituents as indicated above.

The nitro group or groups in the resulting compound of Formula XIII are converted into diazonium groups by reduction and diazotizing. Thereafter, the diazonium group or groups are transformed into the substituents R$_3$ and R$_4$ by methods known per se, such as the Sandmeyer reaction, or by desamination. Then the protecting group R$_{12}$ is split off by hydrogenolysis. If desired, the substituent R$_{10}$ may be converted into the amino group.

Furthermore, compounds of Formula I can be obtained by introducing iodine into a compound of Formula XIV

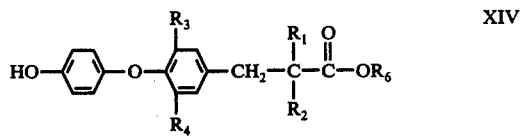

XIV wherein

R$_1$ to R$_4$ and R$_6$ represent the same substituent as indicated above.

Iodination to introduce one or two iodine atoms into the molecule is preferably effected in alkaline solution by means of iodine and or other iodizing agents, such as iodine/potassium iodide, N-iodo acetamide, N-iodo succinimide, iodine chloride, p-toluene sulfonic acid iodo-amide potassium, and the like.

The compounds of Formula XIV are obtained, for instance, by reacting the corresponding acid, its salts, or a reactive derivative thereof with a compound of Formula III following in principle the method described for the preparation of the compounds of Formula II.

The compounds of Formula XIV can also be obtained by condensing a reactive ester, preferably the p-tosyl-ester, of a compound of Formula XI with a compound of Formula XV.

XV wherein

R$_{12}$ represents the same substituent as indicated above, in the presence of a solvent and/or an inorganic or organic base, preferably pyridine, if required, at elevated temperature to yield a compound of formula XVI

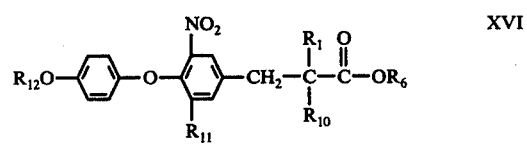

XVI wherein $R_1$, $R_6$, and $R_{10}$ to $R_{12}$ request the same substituent as indicated above.

The nitro groups in the compounds of Formula XVI are then converted into the substituents $R_3$ and $R_4$, as mentioned above. The substituent $R_{12}$ is split off by hydrogenolysis, preferably in the presence of a noble metal catalyst and the substituent $R_{10}$ is converted, if desired, into an amino group.

The compounds of Formula XIV can also be obtained by reacting a compound of Formula IX with a compound of Formula XVII

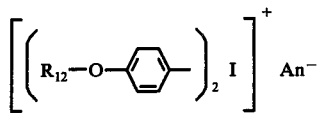   XVII wherein
  $R_{12}$ represents the same substituent as indicated above and
  $An^-$ represents an anion,
in the presence of a basic substance, preferably in the presence of a metal alcoholate, suitably by using an alcohol as solvent and by removing from the resulting compound of Formula XVIII

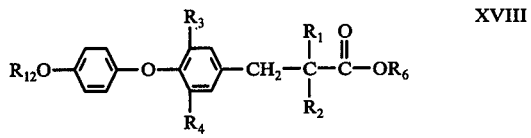   XVIII wherein
  $R_1$ to $R_4$, $R_6$, and $R_{12}$ represent the same substituents as indicated above,
the substituent $R_{12}$ by hydrogenolysis.

When compounds of Formula I in which $R_2$ indicates an acylated amino group are to be prepared, it is also possible to acylate the amino group in compounds of Formula I wherein $R_2$ represents an amino group, as obtained according to one of the procedures described above, by reacting with a reactive derivative of a carboxylic acid, such as an anhydride, an acid halide, or an ester, by methods known per se.

If desired, compounds of Formula I can be converted to the corresponding salts by adding bases or acids. Using optically active bases or acids, the corresponding optically active salts can be resolved into optically active isomers—as mentioned before—by methods known per se.

The following examples serve to illustrate the present invention without, however, limiting the same thereto. The melting and boiling points given are uncorrected. In performing the examples, maximum yields were not intended to be obtained.

EXAMPLE 1

7.91 g. of α-methyl thyroxine are suspended in 150 cc. of ethanol. While heating, the solution is saturated with dry hydrogen chloride. Thereafter, the solvent is distilled off at reduced pressure. The residue is dissolved in a mixture of ethanol and water (1:1). Adding a 5% solution of sodium hydrogen carbonate in water, the ethyl ester of α-methyl thyroxine precipitates; melting point: 156°–157° C. after recrystallization from ethanol. The yield is 6.05 g., i.e. 74% of the theoretical yield.

EXAMPLE 2

On following the procedure as described in example 1 and using methanol as the esterifying reactant, the methyl ester of α-methyl thyroxine is obtained; melting point: 123°–125° C. after recrystallization from methanol. The yield is 85% of the theoretical yield.

EXAMPLE 3

2 g. of α-methyl thyroxine are added in portions to a mixture of 20 cc. of benzyl alcohol and 5 g. of polyphosphoric acid, warmed to 95° C. While stirring, the clear solution is heated to 95° C. for 4 hours. After cooling, the solution is poured into 200 cc. of ice water and extracted with ether. The ether solution is washed with a solution of 1% ammonia in water, dried over sodium sulfate and the solvent is distilled off under reduced pressure. The residue is dissolved in ethanol. On addition of water, the benzyl ester of α-methyl thyroxine precipitates; melting point: 178°–180° C. after recrystallization from n-butanol.

EXAMPLE 4

5.7 g. of the 3,5-di-iodo-α-methyl thyroxine ethyl ester are dissolved in a mixture of 60 cc. of butylamine and 120 cc. of ethanol. A solution of 5.1 g. of iodine in 120 cc. of ethanol is added drop by drop while stirring. Stirring is continued for 1 more hour. The solution is then cooled with ice and neutralized by adding concentrated hydrochloric acid thereto. On addition of a solution of sodium acetate, α-methyl thyroxine ethylester precipitates; melting point: 156°–157° C. The yield is 83% of the theoretical yield. The compound is identical with that of example 1. The starting material 3,5-di-iodo-α-methyl thyronine ethyl ester used in the preceding example is obtained as follows:

11.8 g. of 3,5-di-iodo-α-methyl thyronine are suspended in 240 cc. of absolute ethanol. While cooling, the solution is saturated with dry hydrogen chloride. While introduction of hydrogen chloride is continued, the solution is refluxed for several hours. The resulting clear solution is distilled to dryness under reduced pressure. The residue is dissolved in a mixture of ethanol/water (1:1) and neutralized by adding an aqueous 5% sodium hydrogen carbonate solution. The 3,5-di-iodo-α-methyl thyronine ethyl ester precipitates; melting point: 152°–154° C. The yield is 73% of the theoretical yield.

EXAMPLE 5

On following the procedure described in example 1, the 3,5,3'-tri-iodo-α-methyl thyronine ethyl ester is obtained by using 3,5,3'-tri-iodo-α-methyl thyronine as starting material; melting point: 177.5°–180° C. after recrystallization from ethanol. The yield is 78.5% of the theoretical yield.

The starting material 3,5,3'-tri-iodo-α-methyl thyronine is obtained as follows:

5.4 g. of 3,5-di-iodo-α-methyl thyronine are dissolved in a mixture of 26 cc. of 1 N sodium hydroxide solution and 108 cc. of water. A solution of 3.15 g. of p-toluene sulfonic acid-iodo-amide potassium in 53 cc. of water is added drop by drop thereto at room temperature. After stirring for some time, 95% acetic acid is added in an amount sufficient to adjust the pH-value to a pH of 6.0. The resulting precipitate is filtered off by suction and dissolved in a mixture of 25 cc. of 2 N sodium hydroxide solution and 62 cc. of ethanol. The solution is purified by means of activated charcoal. Thereafter, while heating to boiling, 2 N hydrochloric acid is added in an amount sufficient to adjust the pH value to a pH of 6.0. The precipitate is filtered off by suction, washed with ethanol/water (1:2) and dried under reduced pressure at 100° C. The resulting 3,5,3'-tri-iodo-α-methyl thyronine has a melting point of 260°-264° C. The yield is 66% of the theoretical yield.

EXAMPLE 6

On following the procedure described in example 1 and using α-ethyl thyroxine as starting material, the ethyl ester of α-ethyl thyroxine is obtained; melting point: 138°-140° C. The yield is 72% of the theoretical yield.

The starting material α-ethyl-thyroxine is obtained as follows:

35.6 g. of 1-p-methoxy phenyl butanone-(2), 19.5 g. of potassium cyanide, and 62.5 g. of ammonium carbonate are suspended in 330 cc. of 50% ethanol and are heated to 65°-70° C. for 7 hours while stirring. On cooling and, if necessary, after introducing carbon dioxide, 5-ethyl-5-(4-methoxy benzyl) hydantoin crystallizes in white crystals of a melting point of 191°-193° C. after recrystallization from ethanol/water. The yield is 90% of the theoretical yield.

24.8 g. of said compound are heated under reflux in 110 cc. of 57% aqueous hydriodic acid for 2 hours. On cooling, 5-ethyl-5-(4-hydroxy benzyl) hydantoin of the melting point of 290°-291° C. is obtained. The yield is 68% of the theoretical yield.

23.4 g. of said compound are added in portions to 80 cc. of nitric acid (d = 1.42) at 35°-37° C. while stirring vigorously. Stirring is continued for 2 hours and the solution is diluted with 200 cc. of ice water. 5-Ethyl-5-(3,5-dinitro-4'-hydroxy benzyl) hydantoin precipitates in crystalline form; melting point: 236°-238° C. after recrystallization from ethanol. The yield is 70% of the theoretical yield.

64.8 g. of said compound and 42.0 g. of p-toluene sulfochloride are dissolved in 150 cc. of pyridine and heated under reflux for 10 minutes. The solution is cooled to room temperature. A solution of 62 g. of hydroquinone monomethyl ether in 62 cc. of pyridine is added thereto. The mixture is heated under reflux for one hour and six times its volume of ice water is admixed. 5-Ethyl-5-[3,5-dinitro-4-(4'-methoxy phenoxy) benzyl] hydantoin is obtained; melting point: 195°-197° C. after recrystallization from diluted acetic acid. The yield is 93% of the theoretical yield.

43 g. of said compound are dissolved in a mixture of 300 cc. of methanol and 100 cc. of tetrahydrofuran and are hydrogenated with hydrogen with the addition of Raney-Nickel catalyst at atmospheric pressure and room temperature. Thereafter, the catalyst is filtered off and the solvent is distilled off at reduced pressure. The residue is recrystallized from ethyl acetate/petroleum ether and 5-ethyl-5-[3,5-diamino-4-(4'-methoxy phenoxy) benzyl] hydantoin is obtained; melting point: 207°-208° C. The yield is 77.5% of the theoretical yield.

37.0 g. of said compound, dissolved in 80 cc. of glacial acetic acid, are added drop by drop to 40 cc. of concentrated sulfuric acid at 10° C. The resulting solution is added drop by drop to a cooled solution of 17.5 g. of sodium nitrite in a mixture of 175 cc. of concentrated sulfuric acid and 200 cc. of glacial acetic acid while stirring. Stirring is continued at a temperature of 0° C. for 1 more hour. The solution is then added rapidly to a mixture of 87 g. of potassium iodide, 68.0 g. of iodine, and 10.0 g. of urea in 1300 cc. of water to which 450 cc. of chloroform are admixed, while stirring vigorously. Stirring is continued for 2 more hours. The chloroform layer is separated and the aqueous layer is extracted several times with chloroform. The chloroform extracts are combined, washed with a solution of sodium bisulfite in water and then with water, and dried over sodium sulfate. After filtration, the solvent is distilled off under reduced pressure and 5-ethyl-5-[3,5-di-iodo-4-(4'-methoxy phenoxy) benzyl] hydantoin is obtained; melting point: 241°-243° C. The yield is 73% of the theoretical yield.

59.2 g. of said compound are heated under reflux in a mixture of 180 cc. of 57% hydriodic acid and 180 cc. of glacial acetic acid for one hour. On cooling, 5-ethyl-5-[3,5-di-iodo-4-(4'-hydroxy phenoxy) benzyl] hydantoin precipitates; melting point: 313°-316° C. after recrystallization from ethanol. The yield is 93.7% of the theoretical yield.

115.6 g. of said compound are dissolved in 2,200 cc. of 2 N sodium hydroxide solution and heated in an autoclave at 140° C. for 100 hours. 16% hydrochloric acid is added to the hot solution in an amount sufficient to adjust the pH-value to a pH of 7.0. The precipitate is filtered off by suction from the hot solution. The major part of it is α-ethyl-3,5-di-iodo thyronine. α-Ethyl-3-iodo thyronine crystallizes on cooling the filtrate. Both precipitates are purified by dissolving them in a mixture of alcohol and hydrochloric acid, treating the solution with charcoal, and precipitating the amino acid by means of a saturated solution of sodium acetate. α-Ethyl-3,5-di-iodo thyronine of the melting point: 285°-288° C. is obtained in a yield of 46.6% of the theoretical yield, and α-ethyl-3-iodo thyronine of the melting point: 210°-215° C. is obtained in a yield of 39% of the theoretical yield, α-Ethyl-3-iodo thyronine solidifies on further heating at 220°-240° C. and melts thereafter at 281°-283° C. under decomposition.

22.1 g. of α-ethyl-3,5-di-iodo thyronine are dissolved in 130 cc. of a 33% solution of ethylamine in water and 86.5 cc. of a 1.85 N solution of potassium iodide and iodine are added drop by drop to the above described solution while stirring. Stirring is continued for one more hour and 16% hydrochloric acid is added in an amount sufficient to adjust the pH value to a pH of 5.0. The precipitate is filtered off, washed with water, and dissolved in 250 cc. of ethanol with the addition of 100 cc. of 2 N sodium hydroxide solution. The solution is purified by means of charcoal and is acidified with 2 N hydrochloric acid to a pH of 6.0. α-Ethyl thyroxine, melting at 236°-238° C. is obtained in a yield of 60% of the theoretical yield.

EXAMPLE 7

On following the procedure described in example 1 and using α-n-propyl thyroxine as starting material, the ethyl ester of α-n-propyl thyroxine of the melting point: 174°-176° C. is obtained. The yield is 57% of the theoretical yield.

The starting material α-n-propyl thyroxine is obtained on following the procedure described in example 6, but using the following intermediates:

5-n-Propyl-5-(4-methoxy benzyl) hydantoin, melting point: 244°-245° C. after recrystallization from ethanol. Yield: 63% of the theoretical yield.

5-n-Propyl-5-(4-hydroxy benzyl) hydantoin, melting point: 286°–288° C. after recrystallization from ethanol. Yield: 90% of the theoretical yield.

5-n-Propyl-5-(3,5--dinitro-4-hydroxy benzyl) hydantoin, melting point: 212°–213° C. after recrystallization from glacial acetic acid. Yield: 74% of the theoretical yield.

5-n-Propyl-5-[3,5-dinitro-4-(4'-methoxy phenoxy) benzyl]hydantoin, melting point: 196°–198° C. after recrystallization from diluted acetic acid. Yield: 55% of the theoretical yield.

5-n-Propyl-5-[3,5-diamino-4-(4'-methoxy phenoxy) benzyl]hydantoin. Yield: 96% of the theoretical yield.

5-n-Propyl-5-[3,5-di-iodo-4-(4'-methoxy phenoxy) benzyl]hydantoin, melting point: 247°–248° C. after recrystallization from methanol/2-ethoxy ethanol.

5-n-Propyl-5-[3,5-di-iodo-4-(4'-hydroxy phenoxy) benzyl]hydantoin, melting point: 298°–299° C. after recrystallization from ethanol. Yield: 80% of the theoretical yield.

α-n-Propyl-3,5-di-iodo thyronine, melting point: 278°–280° C. Yield: 58% of the theoretical yield.

α-n-Propyl thyroxine, melting point: 231°–232° C. Yield: 46.5% of the theoretical yield.

EXAMPLE 8

On following the procedure described in example 1 and using (+)-α-methyl thyroxine as starting material, the ethyl ester of (+)-α-methyl thyroxine, melting point: 156°–158° C. is obtained. The yield is 84% of the theoretical yield.

$[\alpha]_D^{29} = +11.0°$ (concentration = 2% in acetic acid)

The (−)-α-methyl thyroxine ethyl ester is obtained in the same manner by using (−)-α-methyl thyroxine as starting material.

The optically active amino acids used as starting materials are obtained as follows:

53.9 g. of α-methyl-3,5-di-iodo thyronine are dissolved in 270 cc. of concentrated formic acid with the addition of 27 cc. of acetic acid anhydride. After standing for some time the N-formyl-α-methyl-3,5-di-iodo thyronine is obtained in white crystals. The precipitate is filtered off by suction, washed with water until free of formic acid, and dried. The yield is 45.5 g. Yield: 80% of the theoretical yield. Melting point: 221°–223° C.

56.7 g. of said compound are suspended in 560 cc. of absolute isopropanol and refluxed. A solution of 47.3 g. of (−)brucine, in 240 cc. of absolute isopropanol, also heated to reflux, is added. The solution is refluxed for some time. The (−) brucine salt of (+)-N-formyl-α-methyl-3,5-di-iodo thyronine precipitates in white crystals and is filtered off by suction from the hot solution. The (−) brucine salt of (−)-N-formyl-α-methyl-3,5-di-iodo thyronine precipitates from the filtrate. It is dissolved in 200 cc. of N ammonia and extracted several times with chloroform. The aqueous layer is neutralized by the addition of hydrochloric acid while cooling. Thereby, (−)-N-formyl-α-methyl-3,5-di-iodo thyronine precipitates. Melting point: 234°–236° C. after recrystallization from aqueous isopropanol. The yield is 74% of the theoretical yield.

$[\alpha]_D^{23}$ −24° (concentration = 5% in 95% ethanol).

The (−)-brucine salt of (+)-N-formyl-α-methyl-3,5-di-iodo thyronine is recrystallized from dimethyl formamide/acetic acid ethyl ester. It has a melting point of 258°–262° C. The salt is converted into the free acid by following the procedure described for the (−) isomer. Melting point: 234°–236° C. after recrystallization from isopropanol. The yield is 90% of the theoretical yield.

$[\alpha]_D^{22} = +24.2°$ (concentration = 5% in 95% ethanol).

14.3 g. of (−)-N-formyl-α-methyl-3,5-di-iodo thyronine are dissolved in 150 cc. of 16% hydrobromic acid and refluxed for 3 hours. On cooling, the hydrobromide precipitates and is filtered off. It is dissolved in 70% ethanol and (−)-α-methyl-3,5-di-iodo thyronine is obtained by precipitation with sodium acetate solution as described for the racemate. Melting point: 285°–288° C. The yield is 89% of the theoretical yield.

$[\alpha]_D^{22} = −14.6°$ (concentration = 5% in N hydrochloric acid/ethanol 1:2).

On following the procedure described above, the (+)-α-methyl-3,5-di-iodo thyronine is obtained from (+)-N-formyl-α-methyl-3,5-di-iodo thyronine in an analogous manner. Melting point: 286°–288° C. The yield is 86% of the theoretical yield.

$[\alpha]_D^{25} = +14.5°$ (concentration = 5% in N-hydrochloric acid-ethanol 1:2).

On following the procedure described in example 6 for the racemate, (+)-α-methyl-thyroxine is obtained from said (+)-α-methyl-3,5-di-iodo thyronine. Melting point: 273°–274° C. The yield is 84% of the theoretical yield.

$[\alpha]_D^{29} = +10°$ (concentration = 5% in N hydrochloric acid/95% ethanol 1:2).

EXAMPLE 9

On following the procedure described in example 5, the optically active ethyl esters of α-methyl-3,5,3'-tri-iodo thyronine are obtained using the corresponding optically active starting materials.

(+)-α-Methyl-3,5,3'-tri-iodo thyronine ethyl ester; yield: 67% of the theoretical yield.

$[\alpha]_D^{24} = +12.0°$ (concentration = 2% in acetic acid).

(−)-α-Methyl-3,5,3'-tri-iodo thyronine ethyl ester; yield: 52% of the theoretical yield.

$[\alpha]_D^{29} = −11.1°$ (concentration = 2% in acetic acid).

The optically active starting materials, obtained according to example 5, are as follows:

(−)-α-Methyl-3,5,3'-tri-iodo thyronine; melting point: 281°–283° C.

$[\alpha]_D^{23} = −12.8°$ (concentration = 5% in N hydrochloric acid/ethanol 1:2).

(+)-α-Methyl-3,5,3'-tri-iodo thyronine; melting point: 277.5°–278° C.

$[\alpha]_D^{22} = +13.0°$ (concentration = 5% in N hydrochloric acid/ethanol 1:2).

In place of the methyl, ethyl, and benzyl esters of the racemic or optically active α-methyl, α-ethyl, or α-n-propyl thyroxine or 3,5,3'-tri-iodo thyronine, there may be obtained other lower alkyl esters of said compounds such as the n-propyl, isopropyl, n-butyl, isobutyl, tertiary butyl, n-amyl, isoamyl, n-hexyl esters, or cycloalkyl esters such as the cyclopentyl, cyclohexyl, methyl cyclohexyl esters, or other aralkyl esters such as the phenyl ethyl, o-methyl benzyl, p-methyl benzyl esters of α-alkyl thyroxine or α-alkyl-3,5,3'-tri-iodo thyronine by using corresponding starting materials and reactants as described in the preceding examples.

These alkyl, cycloalkyl, or aralkyl esters of α-alkyl thyroxine or 3,5,3'-tri-iodo thyronine may be substituted in their alkyl, cycloalkyl, or aralkyl ester moiety of the molecule, for instance, by the hydroxyl group, the esterified hydroxyl group, and especially by an amino group. Such compounds are, for instance, the monoglycol ester, the β-acetoxy ethyl ester, the 4-hydroxy cyclohexyl ester, the 4-acetoxy benzyl ester of α-ethyl thyroxine or α-methyl-3,5,3'-tri-iodo thyronine, and others. Especially valuable compounds are the compounds in which the ester moiety is substituted by amino group. Such compounds are, for instance, the β-amino ethyl ester, the β-dimethylamino ethyl ester, the -di-n-butylamino-n-butyl ester, the 4-dimethylamino benzyl ester, the β-piperidino ethyl ester, the γ-pyrrolidino-n-propyl ester, the morpholino methyl ester, the β-piperazino ethyl ester, the β-(4-methyl piperazino) ethyl ester of α-methyl. thyroxine or α-ethyl-3,5,3'-tri-iodo thyronine, and others.

Likewise, such alkyl, cycloalkyl, or aralkyl esters can be prepared from other α-alkyl substituted thyroxine or 3,5,3'-tri-iodo thyronine compounds such as α-isopropyl, α-butyl, α-isobutyl, α-tertiary butyl, α-n-amyl, α-isoamyl, α-n-hexyl substituted thyroxine or 3,5,3'-tri-iodo thyronine compounds.

In place of the N-formyl-α-alkyl substituted thyronine compounds, there may be used other N-acyl-α-alkyl substituted thyronine compounds such as the N-acetyl, N-benzoyl compounds and others.

As stated above, the new esters of α-alkyl thyroxine or α-alkyl-3,5,3'tri-iodo thyronine compounds from addition salts with inorganic and organic acids. When using these compounds therapeutically, such salts are formed with pharmaceutically acceptable inorganic acids such as hydrochloric acid, hydrobromic acid, phosphoric acid, sulfuric acid, and others, or organic acids such as acetic acid, propionic acid, malonic acid, maleic acid, succinic acid, tartaric acid, citric acid, malic acid, sorbic acid, benzoic acid, salicylic acid, nicotinic acid, isonicotinic acid, and others.

The new esters have proved to be highly effective drugs for the treatment of thyroid gland deficiencies such as hypothyroidism, myxedema, cretinism and mental retardation when associated with such thyroid deficiency, amenorrhea and female hypogonadism if due to such thyroid deficiency, simple goiter, and other conditions caused by such thyroid deficiencies. In contrast to other thyroid hormone preparations they have proved to be especially useful in the treatment of arteriosclerosis and particularly of coronary sclerosis because they have a pronounced effect upon the cholesterol and lipid blood level which is lowered considerably. Their great advantage over thyroid hormones is that they do not increase the basal metabolic rate and do not exhibit thyrotoxic activity.

As stated above, the new esters according to the present invention have the great advantage over known drugs of the thyronine type that they can be administered not only parenterally but also orally without losing their effectiveness and without causing undesired side-effects such as stenocardia. The new esters are orally administered in a dosage between about 1 mg./daily and about 25 mg./daily, depending upon the ester used. dl-α-Methyl thyroxine ethyl ester, for instance, given orally in an amount of 10 mg./daily reduced the serum cholesterol level of a patient from 288 to 200 mg.% within 14 days.

The following examples serve to illustrate the preparation of compositions containing the new esters according to the present invention as they are used in therapy.

EXAMPLE 10

10.0 g. of d,l-α-methyl thyroxine ethyl ester, 59.25 g. of spray-dried lactose, 40.0 g. of microcrystalline cellulose, 10 g. of dried corn starch, and 0.75 g. of magnesium stearate are intimately mixed with each other and are compressed, without preceding granulation, to tablets of a diameter of 7 mm. and a weight of about 120 mg. Each table contains 10 mg. of the dl-α-methyl thyroxine ethyl ester.

EXAMPLE 11

The mixture of ingredients described in example 10 is compressed to biconvex dragee cores which are then sugar coated in rotating coating and polishing pans to the desired dragee size. Each dragee contains 10 mg. of d,l-α-methyl thyroxine ethyl ester.

EXAMPLE 12

10.0 g. of d,l-α-methyl-3,5,3'-tri-iodo thyronine ethyl ester are intimately mixed with 117.0 g. of dibasic calcium phosphate $CaHPO_4 \cdot 2H_2O$, 6.6 g. of liquid paraffin (paraffinum perliquidum), and 0.5 g. of magnesium stearate. The resulting mixture is sieved and the powder is filled into gelatin capsules. Each capsule contains about 130 mg. of the powder with 10 mg. of said d,l-α-methyl-3,5,3'-tri-iodo thyronine ethyl ester.

Of course, many changes and variations in the starting and intermediate compounds, in the reaction conditions, temperature, and duration, in the solvents, condensing agents, catalysts, and other reactants used, in the methods of working up the reaction mixture and of isolating and purifying the reaction products, in the preparation of pharmaceutical compositions containing such compounds, and the like may be made by those skilled in the art in accordance with the principles set forth herein and in the claims annexed hereto.

The compounds of the invention are especially noteworthy as described above, for their lipid-controlling, including their cholesterol-controlling properties. The D,L-alpha-methyl-thyroxine ethyl ester and especially its salts with inorganic acids like hydrochloric acid is especially remarkable for its property to lower the level of cholesterol and also of triglycerides in warm blooded animals. These properties were further confirmed in clinical work on patients suffering from abnormalities in their lipid blood level such as occur in patients suffering from diabetes and also in patients afflicted with secondary lipid level abnormalities, as occur in patients suffering from malfunction of the liver, pancreas, thyroid gland, heart or other organic body.

The D,L-alpha-methyl-thyroxine ethyl ester was effective to lower the triglyceride level upon administration to patients for 8 weeks in dosages from about 20 to 40 mg daily. The triglyceride level was reduced to normal. When the treatment was discontinued, and the ester replaced by placebo administration, the triglyceride level increased abnormally again and was brought again under control by renewed administration of the ester. Typically, the hydrochloride salt of the above-named ester decreased the triglyceride level from 219 to 181 mg/100 ml and from 206 to 154 mg/100 ml, after placebo interrupted treatment (20 mg/daily dosage); and from 208 to 145 mg/100 ml and to 181 mg/100 ml, after placebo interrupted treatment (40 mg/daily dosage). Likewise, abnormally high cholesterol level was controlled by administration of the ester. The ester was preferably administered as the addition salt of an inorganic acid, especially the hydrochloride salt.

All clinical work was carried out in accordance with professionally accepted medical practices. No adverse side effects were obserbed even in the comparatively high dosages used. The compositions as described above comprising the ester were administered orally. The dosage varies from the amount effective to control the cholesterol and triglyceride level at the rate prescribed by the physician to that at which no further benefits on the condition treated are observed, which may vary under the circumstances. A dosage in the range of about 10 to about 50 mg daily has been found satisfactory.

We claim:

1. A pharmaceutical composition suitable for controlling the cholesterol and triglyceride blood level in a human comprising D, L-alpha-methyl-thyroxine ethyl ester in a pharmaceutically acceptable carrier said ester being present in an amount sufficient to control the cholesterol and triglyceride blood level.

2. The composition of claim 1 wherein the thyroxine is the hydrochloride salt thereof.

3. The composition of claim 2 wherein said thyroxine ester is present in an amount of 10 to 50 mg.

4. The composition of claim 1 wherein said thyroxine ester is present in an amount of from about 10 to about 50 mg.

5. The composition of claim 1 wherein said thyroxine ester is present in an amount of from about 20 to about 40 mg.

6. The composition of claim 2 wherein said thyroxine ester is present in an amount of from about 20 to about 40 mg.

7. The composition of claim 1 wherein said thyroxine ester is present in an amount of about 20 mg.

8. The composition of claim 2 wherein said throxine ester is present in an amount of about 20 mg.

9. The compositon of claim 1 which is a tablet, dragee or capsule.

10. The composition of claim 2 which is a tablet, dragree or capsule.

11. A method of controlling the cholesterol and triglyceride level in a human which comprises administering orally to said human a pharmaceutical composition comprising D-L-alpha-methyl-throxine ethyl ester in a pharmaceutically acceptable carrier in an amount effective to control the cholesterol and triglyceride blood level.

12. The method of claim 11 of controlling the cholesterol and triglyceride level in a human comprising administering said composition orally to said human in a total amount of from about 20 to about 40 mg per day to said human until said control is realized.

13. The method of claim 11 wherein the amount of thyroxine ester administered is from about 10 to about 50 mg.

14. The method of claim 11 wherein the amount of thyroxine ester administered is about 40 mg.

15. The method of controlling the cholesterol and triglyceride level in a human by administering orally to said human the composition of claim 1 in an amount of 20 to 40 mg.

16. The method of claim 11 wherein the administration is carried out daily until said control is achieved.

17. The method of claim 11 wherein the thyroxine ester administered is the hydrochloride salt thereof.

18. The method of claim 17 wherein the administration is carried out daily until said control is achieved.

19. The method of claim 13 wherein the thyroxine ester is the hydrochloride salt thereof.

* * * * *